United States Patent [19]

Shiomi et al.

[11] Patent Number: 5,536,888
[45] Date of Patent: Jul. 16, 1996

[54] PROCESS FOR PRODUCING DIOL COMPOUNDS

[75] Inventors: Yasushi Shiomi; Hiroyuki Fukushima; Toshihiko Sumida; Shinichi Furusaki, all of Ube, Japan

[73] Assignee: UBE Industries, Ltd., Yamaguchi, Japan

[21] Appl. No.: 364,712

[22] Filed: Dec. 27, 1994

[30] Foreign Application Priority Data

Dec. 28, 1993 [JP] Japan .................................. 5-337648
Dec. 28, 1993 [JP] Japan .................................. 5-337655

[51] Int. Cl.$^6$ .......................... C07C 29/149; C07C 31/20
[52] U.S. Cl. .......................... 568/864; 502/343; 564/468; 564/503; 568/885
[58] Field of Search .................................. 568/864, 885; 564/468, 503

[56] References Cited

U.S. PATENT DOCUMENTS

| | | |
|---|---|---|
| 2,079,414 | 5/1937 | Lazier . |
| 2,617,835 | 11/1952 | Curtin .................................. 568/864 |
| 3,524,892 | 8/1970 | Horlenko et al. . |
| 4,918,248 | 4/1990 | Hattori et al. .................................. 568/864 |
| 5,142,067 | 8/1992 | Wegman et al. .................................. 568/864 |
| 5,364,986 | 11/1994 | Demmering et al. .................................. 568/864 |
| 5,386,066 | 1/1995 | Schneider et al. .................................. 568/885 |

FOREIGN PATENT DOCUMENTS

| | | |
|---|---|---|
| 516096 | 8/1955 | Canada .................................. 568/864 |
| 4103490 | 9/1992 | Germany . |
| 1062335 | 3/1967 | United Kingdom . |

OTHER PUBLICATIONS

Patent Abstracts of Japan, vol. 006 No. 219 (C-132), 2 Nov. 1982 & JP-A-57 122941 (Ube Kosan) 31 Jul. 1982.

*Primary Examiner*—Joseph E. Evans
*Attorney, Agent, or Firm*—Burgess, Ryan and Wayne

[57] ABSTRACT

A diol compound, for example, hexanediol, is produced with a high efficiency by esterifying a carboxylic acid mixture, collected from a reaction product mixture of a liquid phase oxidation of cyclohexane, with an esterifying agent and hydrogenate-decomposing the resultant esterification product mixture with hydrogen. The hydrogenate-decomposition is carried out by using a specific catalyst free from chromium and including a member selected from (A) copper and zinc-containing catalytic materials which are prepared by mixing an aqueous solution of water-soluble copper and zinc salts with an aqueous alkali metal or ammonium carbonate or alkali metal or ammonium hydrogen carbonate solution, reducing the resultant precipitate comprising a basic copper and zinc carbonate mixture with hydrogen and partially oxidizing the resultant reduction product with an oxygen-containing gas, and (B) copper and zinc-containing catalytic materials which are prepared by conducting the same mixing procedure as that for the catalytic material (A) except that the mixing is carried out at a temperature of 60° to 95° C. at a pH of 6.5 to 9.0, and by calcining the resultant precipitate at a temperature of 300° C. to 450° C.

18 Claims, No Drawings

PROCESS FOR PRODUCING DIOL COMPOUNDS

BACKGROUND OF THE INVENTION

1. Field of the Invention

The present invention relates to a process for producing diol compounds, for example, 1,6-hexanediol, 1,5-pentanediol and 1,4-butanediol by esterifying a carboxylic acid mixture collected from a reaction product mixture liquid of a liquid phase oxidation of cyclohexane with, for example, air, and then hydrogenate-decomposing the resultant esterification product. These diol compounds are useful as polyurethane elastomers, as additives for synthetic resins and as intermediates of medicines and agricultural chemicals.

2. Description of Related Art

As disclosed in Japanese Examined Patent Publication Nos. 49-27,164 and 53-33,567, cyclohexanol and cyclohexanone, which are useful as materials for the synthesis of ε-caprolactam, are industrially produced by a liquid phase oxidation of cyclohexane with air, and diols, for example, 1,6-hexanediol, are produced by esterifying a carboxylic acid mixture obtained as a by-product of the above-mentioned oxidation reaction with an alcohol, and then hydrogenate-decomposing the resultant esterification product with hydrogen.

In the conventional process for producing diol compounds, a copper-chromium-containing catalyst is commonly employed as a hydrogenation catalyst.

The conventional copper-chromium-containing catalyst contains chromium, which is harmful, and thus when this catalyst is used, specific dust-preventing means are necessary while handling the catalyst. Also, the conventional chromium-containing catalyst is disadvantageous in that specific equipment is necessary for the treatment of discharged water and waste liquid. Especially, where the reaction is carried out in a liquid phase suspension state, since the catalyst partially dissolves in the reaction liquid, it is difficult to treat the residue in a distillation column after the diol compounds, for example, 1,6-hexanediol, are collected from the reaction product mixture liquid by distillation.

Accordingly, various chromium-free catalysts have been evaluated for the process for producing alcohol compounds by hydrogenate-decomposing carboxylic acid esters with hydrogen. However, these conventional catalysts are not industrially satisfactory for the production of diol compounds, for example, 1,6-hexanediol.

For example, Japanese Examined Patent Publication (Kokoku) No. 58-4 50775 discloses a process for producing alcohols from corresponding methyl esters of coconut oil fatty acids by using a catalyst comprising copper oxide and iron oxide carried on aluminum oxide. However, when this catalyst is applied to the production of 1,6-hexanediol, this catalyst exhibits a significantly lower activity than that of the conventional copper-chromium-containing catalyst, whereas the filter-separability of this catalyst is similar to that of the conventional copper-chromium-containing catalyst.

Also, Japanese Unexamined Patent Publication (Kokai) No. 63-141937 discloses a process for producing lauryl alcohol from methyl laurate by using a catalyst consisting of copper oxide and zinc oxide. When this catalyst is applied to the production of 1,6-hexanediol, however, this catalyst has the disadvantage that its filter-separability is very poor, whereas the activity of the catalyst is higher than that of the conventional copper chromium-containing catalyst.

Further, Japanese Unexamined Patent Publication (Kokai) No. 61-2016 discloses a copper and zinc-containing hydrogenation catalyst usable for the production of ethylene glycol. This catalyst is prepared by adding an alkali solution to an aqueous solution containing copper ions and zinc ions at room temperature at a pH of 3 to 7, calcining the resultant precipitate and reducing the calcining product. When this type of catalyst is applied to the preparation of diol compounds, it has the disadvantage that its filter-separability is poor.

Still further, Japanese Unexamined Patent Publication (Kokai) No. 57-53421 discloses a process for producing propane diol by hydrogenating hydroxypropionaldehyde in the presence of a hydrogenation catalyst prepared by precipitating a crystal mixture containing a copper-zinc complex of the empirical formula:

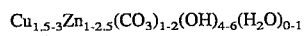

$$Cu_{1.5-3}Zn_{1-2.5}(CO_3)_{1-2}(OH)_{4-6}(H_2O)_{0-1}$$

and aluminium compounds, from an aqueous solution of copper and zinc compounds and an aluminum compound in the presence of a carbonate at a pH of 6.9 to 8.0, and heat-decomposing the crystal mixture at a temperature of 200° C. to 500° C. This catalyst is used in the form of pellets. However, it is not known whether or not this type of catalyst is usable for the production of diol compounds from a carboxylic acid-esterification product. Still further, it is known that a chromium-free hydrogenation catalyst comprising metallic copper, copper oxide and zinc oxide is produced by reducing a mixture of copper oxide and zinc oxide. This type of catalyst is usable for the preparation of methyl alcohol from a synthetic gas, as disclosed in Japanese Unexamined Patent Publication (Kokai) No. 64-26526, and for the synthesis of cumene and ethylbenzene from methylstyrene and acetophenone, as disclosed in DD 218090. This type of catalyst is disadvantageous in that when employed for the production of diol compounds, the catalyst exhibits a poor filter-separability. Also, this type of catalyst commonly exhibits a high reactivity and easily generates heat or ignites when brought into contact with air. Therefore, this catalyst is very difficult and complicated to handle safely.

SUMMARY OF THE INVENTION

An object of the present invention is to provide a process for producing diol compounds at a high industrial efficiency by esterifying a carboxylic acid mixture, collected from a reaction product mixture liquid of a liquid phase oxidation of cyclohexane, with an esterifying alcohol and then hydrogenate-decomposing the resultant esterification product with hydrogen by using a specific hydrogenating catalyst which has an excellent catalytic activity, can be easily separated by filtering, and is free from harmful chromium.

The above-mentioned object can be attained by the process of the present invention for producing diol compounds, which comprises the steps of:

esterifying a carboxylic acid mixture, collected from a reaction product mixture liquid obtained by a liquid phase air oxidation reaction of cyclohexane, with an esterifying alcohol, and hydrogenate-decomposing the resultant esterification product with hydrogen, characterized in that the hydrogenate-decomposition of the esterification product with hydrogen is carried out in the presence of a catalyst comprising at least one member selected from the group consisting of:

(A) a copper and zinc-containing catalytic material prepared by mixing an aqueous solution containing a water-soluble copper salt and a water-soluble zinc salt with an aqueous solution containing at least one member selected from the group consisting of alkali metal carbonates, ammonium carbonate, alkali metal hydrogen carbonates and ammonium hydrogen carbonate to provide a precipitate comprising a water-insoluble basic copper and zinc carbonate mixture, reducing the precipitate with hydrogen, and bringing the resultant reduction product into contact with an oxygen-containing gas and;

(B) a copper and zinc-containing catalytic material prepared by mixing an aqueous solution containing a water-soluble copper salt and a water-soluble zinc salt with an aqueous solution containing at least one member selected from the group consisting of alkali metal carbonates, ammonium carbonate, alkali metal hydrogen carbonates and ammonium hydrogen carbonate to provide a precipitate comprising a water-insoluble basic copper and zinc carbonate mixture, and calcining the precipitate at a temperature of 300° C. to 450° C.

DESCRIPTION OF THE PREFERRED EMBODIMENTS

In the process of the present invention, a diol compound is produced by esterifying a carboxylic acid mixture, collected from a reaction product mixture liquid obtained by a liquid phase air oxidation reaction of cyclohexane, with an esterifying agent and hydrogenate-decomposing the esterification product with hydrogen in the presence of a specific catalyst.

The catalyst is free from chromium and comprises at least one member selected from the group consisting of copper and zinc-containing catalytic materials (A) and (B).

The catalytic material (A) is prepared by the following three steps.

First step: An aqueous solution containing a water-soluble copper salt and a water-soluble zinc salt is mixed with an aqueous solution containing at least one member selected from the group consisting of alkali metal carbonates ammonium carbonate, alkali metal hydrogen carbonates and ammonium hydrogen carbonate to provide a precipitate comprising a water-insoluble basic copper and zinc carbonate mixture.

Second step: The precipitate comprising a basic copper and zinc carbonate mixture is reduced with hydrogen.

Third step: The reduction product is brought into contact with an oxygen-containing gas, to partially oxidize the reduction product.

In the first step of the preparation of the catalytic material (A), the water-insoluble basic copper and zinc carbonate mixture, which is a first precursor of the catalytic material (A), is prepared by mixing an aqueous solution containing water-insoluble copper and zinc carbonates with an aqueous solution of at least one member selected from alkali metal carbonates, ammonium carbonate, alkali metal hydrogen carbonates and ammonium hydrogen carbonate which serves as a precipitant, and collecting the resultant precipitate from the aqueous reaction mixture.

The water-soluble copper and zinc salts are not limited to specific types of salts as long as the salts are soluble in water and capable of being converted to water-insoluble compounds. The copper salts are selected from copper salts of inorganic acids, for example, copper nitrate, copper sulfate, and copper chloride, copper salts of organic acids, for example, copper acetate, and copper amine complexes, for example, tetraamine-copper nitrate complex. The zinc salts are selected from copper salts of inorganic acids, for example, zinc nitrate, zinc sulfate and zinc chloride, zinc salts of organic acids, for example, zinc acetate, and amine-zinc salt complexes, for example, hexaamine-zinc nitrate complex. The alkali metal carbonate includes sodium carbonate and potassium carbonate. The alkali metal hydrogen carbonate includes sodium hydrogen carbonate and potassium hydrogen carbonate.

The mixing ratio of the copper salt to the zinc salt is not limited to a specific range. Preferably, the copper salt and the zinc salts are employed in an atomic ratio Cu/Zn of 1:9 to 9:1, more preferably 2:8 to 7:3, still more preferably 2:8 to 6:4.

The mixing procedure of the aqueous copper and zinc salt solution with the aqueous precipitating medium is preferably carried out at a temperature of 50° C. or more but not more than the refluxing temperature of the mixture, more preferably 60° C. to 95° C. If the mixing temperature is too low, the resultant water-insoluble copper and zinc carbonate mixture may be insufficiently crystallized and thus the resultant catalytic material exhibits unsatisfactory filter-separability and catalytic activity. Also, if the mixing temperature is too high, the resultant basic carbonate precipitate may be contaminated with undesirable hydroxides of copper and zinc, and thus the resultant catalytic material exhibits a reduced catalytic activity for hydrogenation and a low filter-separability.

In the mixing procedure for the catalytic material (A), the pH of the mixed aqueous liquid is preferably maintained at a level of 6.5 to 9.5 by controlling the dropwise mixing rate of the aqueous water-soluble copper and zinc salt solution and the aqueous precipitating medium. If the pH is too low, the resultant water-insoluble basic copper and zinc carbonate mixture may be contaminated with a by-product comprising acid radical anion-containing basic copper and zinc salts, for example, basic copper nitrate and basic zinc sulfate, and thus the resultant catalytic material (A) exhibits an unsatisfactory catalytic activity and a poor filter-separability. If the pH is too high, the precipitate may be produced in a reduced amount and the resultant precipitate may be contaminated with copper oxide, and thus the resultant catalytic material (A) exhibits a reduced filter-separability.

After the mixing procedure is completed, the resultant precipitate is collected by, for example, filtering, rinsing with water and drying in air preferably at a temperature of 100° to 120° C., to obtain a water-insoluble basic copper and zinc carbonate mixture. As a result of an X-ray diffractometry, it was confirmed that the basic copper and zinc carbonate mixture comprises, as a principal component, a double salt of the formula: $(Zn, Cu)_5(CO_3)_2(OH)_6$ which is the same as that of aurichalcite, and a small amount of basic zinc carbonate.

The water-insoluble basic copper and zinc carbonate mixture is reduced with hydrogen, and then brought into contact with an oxygen-containing gas to partially oxidize the reduction reaction product.

In the reducing procedure, the reduction gas may be a pure hydrogen gas or a mixed gas of 1% or more by volume of hydrogen and the balance consisting of an inert diluent gas, for example, nitrogen. If the content of hydrogen in the reducing gas is too low, the time necessary to complete the reduction reaction may become too long. Also, if the hydrogen content in the reduction gas is too high, it may become difficult to remove the heat generated by the reduction reaction and thus the copper is undesirably sintered so as to reduce the catalytic activity of the resultant catalytic material (A). Preferably, the reduction gas comprises 2 to 60% by volume of hydrogen diluted by an inert gas.

In the reducing procedure, the reduction gas is fed preferably at a flow rate of 1 to 100 liter/hr per g of the catalytic material. Also, the reduction temperature is preferably maintained at a level of 100° C. to 400° C., more preferably 120° C. to 350° C. If the reduction temperature is too low, the time necessary to complete the reduction reaction may become too long. Also, if the reduction temperature is too high, the copper may be sintered and the resultant catalytic material (A) may exhibit a reduced catalytic activity.

The reduction product is brought into contact with a molecular oxygen-containing gas to partially oxidize the reduction product. To obtain a catalytic material (A) having a satisfactory catalytic activity and filter-separability for practical use, the partial oxidation is preferably carried out to such an extent that about 10 to 80% of the reduced copper in the reduction product is oxidized to copper oxide. Preferably, this partial oxidation procedure is carried out at room temperature by bringing the reduction product into contact with a mixed gas comprising 0.1 to 5% by volume of oxygen and the balance consisting of an inert gas, for example, nitrogen, or with air, and then with a mixed gas comprising 20% by volume of oxygen and the balance consisting of an inert gas, for example, nitrogen, or with air. This oxidation reaction is an exothermic reaction. Therefore, preferably the oxidation temperature is controlled to a level of not more than 100° C.

The catalytic material (B) is prepared by the following two steps.

First step: An aqueous solution containing a water-soluble copper salt and a water-soluble zinc salt is mixed with an aqueous solution containing at least one member selected from the group consisting of alkali metal carbonates, ammonium carbonate, alkali metal hydrogen carbonates and ammonium hydrogen carbonate at a temperature of 60° C. to 95° C. at a pH of 6.5 to 9.0, to provide a precipitate comprising a water-insoluble basic copper and zinc carbonate mixture.

Second step: The precipitate comprising a basic water-insoluble copper and zinc carbonate mixture is calcined at a temperature of 300° C. to 450° C., for example, in air or in an inert gas, for example, nitrogen gas.

The first step (mixing procedure) of the preparation of the catalytic material (B) is carried out by a procedure similar to that of the first step of the preparation of the catalytic material (A) with the following exceptions.

The mixing atomic ratio of copper to zinc in the aqueous copper and zinc salt solution is not limited to a specific range thereof. Preferably the mixing atomic ratio Cu/Zn is 4:6 to 7:3.

The mixing procedure is carried out at a temperature of 60° to 95° C., preferably 60° C. to 90° C. Also, the mixing procedure is carried out while maintaining the pH of the mixture at a level of from 6.5 to 9.0.

If the mixing temperature is lower than 60° C., the resultant water-insoluble copper and zinc carbonate mixture is insufficiently crystallized and thus the resultant catalytic material (B) exhibits unsatisfactory filter-separability and catalytic activity. Also, if the mixing temperature is higher than 95° C., the resultant basic carbonate precipitate is contaminated with undesirable hydroxides of copper and zinc, and thus the resultant catalytic material (B) exhibits a reduced catalytic activity for hydrogenation and a low filter-separability.

If the pH is less than 6.5, the resultant water-insoluble basic copper and zinc carbonate mixture is contaminated with a by-product comprising acid radical anion-containing basic copper and zinc salts, for example, basic copper nitrate and basic zinc sulfate, and thus the resultant catalytic material exhibits an unsatisfactory catalytic activity and a poor filter-separability. If the pH is more than 9.0, the precipitate is produced in a reduced amount, the resultant precipitate is contaminated with copper oxide, and thus the resultant catalytic material (B) exhibits a reduced filter-separability.

After the mixing procedure is completed, preferably, the mixture liquid is further stirred while maintaining the temperature of the mixture liquid at the same level as the mixing temperature or while allowing the mixture liquid to be cooled, to age the resultant precipitate.

During the aging procedure, the pH of the mixture liquid changes slightly. However, it is not necessary to regulate the pH value.

The resultant precipitate comprising the water-insoluble basic copper and zinc carbonate mixture is collected from the mixture liquid by, for example, filtering, rinsing with water and then drying in air at a temperature of 100° C. to 120° C.

The resultant water-insoluble basic copper and zinc carbonate mixture comprises an aurichalcite type copper-zinc double salt $((Cu, Zn)_5(CO_3)_2(OH)_6)$, as the principal component B, and a small amount of basic zinc carbonate.

In the second step, the dried basic copper and zinc carbonate mixture is calcined at a temperature of 300° C. to 450° C., for example, in air or in an inert gas, for example, nitrogen gas.

The basic copper and zinc carbonate mixture is thermally decomposed at a temperature of about 220° C. or more. When calcined at a temperature of 300° C. to 450° C., the basic copper and zinc carbonate mixture is converted to the corresponding copper and zinc oxide mixture having a high catalytic activity and a satisfactory filter-separability for practical use.

The above-mentioned catalytic materials (A) and (B) are useful as catalysts for producing various types of polyol compounds, higher alcohol compounds and aminoalcohol compounds.

For example, these catalytic material (A) and (B) can be utilized in the following processes.

(1) Production of 1,6-hexanediol from adipic acid diesters, for example dimethyl adipate, diethyl adipate, dipropyl adipate, dibutyl adipate and diesters of adipic acid with dioles, for example, 1,6-hexanediol.

(2) Production of 1,5-pentanediol from glutaric acid diesters, for example, dimethyl glutarate, diethyl glutarate, dipropyl glutarate, dipropyl glutarate and dibutyl glutarate.

(3) Production of 1,4-butanediol from succinic acid diesters, for example, dimethyl succinate, diethyl succinate, dipropyl succinate, and dibutyl succinate.

(4) Production of propyleneglycol from lactic acid esters, for example, methyl lactate, ethyl lactate, propyl lactate and butyl lactate.

(5) Production of ethyleneglycol from oxalic acid diesters, for example, dimethyl oxalate, diethyl oxalate, dipropyl oxalate and dibutyl oxalate, and glycolic acid esters, for example, methyl glycolate, ethyl glycolate, propyl glycolate and butyl glycolate.

(6) Production of higher alcohols from esters of saturated and unsaturated, straight and branched chain carboxylic acids having 6 or more carbon atoms, preferably 6 to 24 carbon atoms, with lower alcohols having 1 to 4 carbon atoms, for example, methyl caproate, ethyl caproate, methyl octoate, ethyl octoate, methyl oleate, ethyl oleate, methyl laurate, ethyl laurate, methyl linolate and ethyl linolate.

(7) Production of polyols or aminoalcohols from carboxylic acid esters having a hydroxyl or amino group.

In the process of the present invention, the carboxylic acid mixture is collected and recovered from an oxidation reaction product mixture liquid obtained in the production of cyclohexanol and cyclohexanone by a liquid phase oxidation of cyclohexane with, for example, air, diluted air, or nitric acid by a water extraction or an alkali rinsing.

For example, as disclosed in Japanese Examined Patent Publication (Kokoku) No. 49-27164, a carboxylic acid mixture which substantially does not contain cyclohexanol, cyclohexane and monobasic acid can be recovered from the oxidation reaction product mixture liquid by separating an aqueous phase fraction comprising, as principal components, mono-basic acids, for example, caproic acid, valeric acid and butyric acid, dibasic acids, for example, adipic acid, glutaric acid and succinic acid and oxyacids, for example, oxycaproic acid, from the oxidation reaction product mixture liquid by a water extraction, and then concentrating the aqueous phase fraction.

Also, as disclosed in Japanese Examined Patent Publication (Kokoku) No. 53-33567, a carboxylic acid mixture comprising, as principal components, dibasic acids, for example, adipic acid, glutaric acid and succinic acid, and oxyacids, for example, oxycaproic acid, can be recovered by rinsing the above-mentioned cyclohexanone-oxidation reaction product mixture liquid with an aqueous sodium hydroxide solution, neutralizing the rinsed liquid with a diluted sulfuric acid, extracting the neutralized liquid with methyl-isobutyl-ketone and then concentrating the extract.

The esterification product usable for the present invention can be easily prepared by esterifying the carboxylic acid mixture separated and recovered by the above-mentioned method and comprising the dibasic acids, for example, adipic acid, glutaric acid and succinic acid and the oxyacids, for example, oxycaproic acid, with an esterifying agent, namely an alcohol to produce esters corresponding to the alcohol. The esterifying alcohol usable for the present invention can be selected from monohydric alcohols, for example, methyl alcohol, ethyl alcohol, propyl alcohol, and butyl alcohol, and diols, for example, 1,4-butanediol, 1,5-pentanediol and 1,6-hexanediol. In this step, 1,6-hexanediol is preferably used, more preferably a hydrogenate-decomposition reaction product mixture liquid derived from the esterification product and containing 50% or more of 1,6-hexanediol, is employed.

The esterifying alcohol is used in an amount of 1.2 to 1.5 times, in terms of hydroxyl group equivalent of the alcohol, the acid value of the carboxylic acid mixture used as a starting material. If this proportion is less than 1.2 times, the esterification reaction rate becomes very low, so that the esterification cannot be completed, and thus the resultant esterification reaction product mixture exhibits too high an acid value and becomes undesirable as a material for the hydrogenate-decomposition reaction. Also, if the proportion is more than 1.5 times, while the esterification reaction is not affected, the total amount of the esterification and hydrogenate-decomposition reaction mixture liquid to be treated becomes large requiring a large treatment apparatus, and thus a large amount of energy becomes necessary to recover the target diol compound.

With respect to the conditions for the esterification reaction, there is no limitation other than the above-mentioned items. Usually, the esterification is carried out preferably at a reaction temperature of 200° to 250° C. to such an extent that the acid value of the reaction mixture liquid becomes 5 mgKOH/g or less, more preferably 2 mgKOH/g or less. This is because when the esterification product has an acid value of 5 mgKOH/g or more, the hydrogenating catalyst is very significantly dissolved in the mixture by the action of acidic substances included in the mixture, and thus exhibits a reduced activity. Since the esterification reaction is an equilibrium reaction, the reaction can be rapidly completed by removing a by-product consisting of water by vaporize-accompanying with an inert gas, for example, nitrogen gas.

In the process of the present invention, the hydrogenate-decomposition reaction is carried out by hydrogenating and decomposing the esterification product produced by the above-mentioned procedures with hydrogen.

Usually, the hydrogenate-decomposition reaction is carried out preferably at a temperature of 250° to 300° C., more preferably 270° to 300° C. under a hydrogen pressure, at the above-mentioned temperature, of 150 to 300 kg/cm$^2$, more preferably 200 to 300 kg/cm$^2$. If the reaction temperature is higher than 300° C., a by-product consisting of water is produced in an undesirably large amount, and if the hydrogen pressure is higher than 300 kg/cm$^2$, the safety of the reaction apparatus must be considered, and thus these conditions are not preferable.

In the process of the present invention, the hydrogenate-decomposing step of the above-mentioned esterification product with hydrogen is carried out in the presence of the specific catalyst comprising at least one member selected from the above-mentioned copper and zinc-containing catalytic materials (A) and (B).

In the process of the present invention, the hydrogenate-decomposing step can be carried out by using a reaction apparatus having a conventional liquid phase suspension bed. Namely, the hydrogenate-decomposing step can be carried out by a batchwise reaction method in which the starting material consisting of the esterification product and the specific catalyst are charged into a pressure-resistive reactor and the charged mixture is heated to the reaction temperature under hydrogen gas pressure, while stirring the mixture. Otherwise, the specific catalyst is suspended in the esterification product, and the resultant suspension is heated under hydrogen gas pressure, and then subjected to a continuous reaction procedure by introducing the suspension into a lower portion of a reactor.

The specific catalyst usable for the present invention is preferably in the form of particles having a size in the range of from 1 to 100 μm and a median size of 15 to 25 μm.

The specific catalyst is employed preferably in an amount of 0.1 to 3.0% by weight, more preferably 0.3 to 1.5% by weight, based on the weight of the esterification product.

After the hydrogenate-decomposition reaction is completed, the target diol compounds are easily collected and isolated from a reaction mixture liquid withdrawn from the reactor by conventional method. For example, the specific hydrogenation catalyst is separated and recovered from the reaction mixture liquid by a filtration apparatus, and then the filtrate is subjected to a distillation procedure under a reduced pressure.

By the above-mentioned procedures, the target diol compounds, for example, 1,6-hexanediol, 1,5-pentanediol and 1,4-butanediol can be obtained.

EXAMPLES

The process of the present invention will be further explained by way of specific examples.

In the examples and comparative examples, a carboxylic acid mixture prepared by extracting a reaction product mixture liquid of a liquid phase air oxidation of cyclohexane with water, in accordance with the method disclosed in Japanese Examined Patent Publication (Kokoku) No. 49-27163, was used. The extracted carboxylic acid mixture contained 26.8% by weight of adipic acid, 31.9% by weight of oxycaproic acid, 6.1% by weight of glutaric acid and 1.2% by weight of succinic acid.

In the preparation of an esterification product, the above-mentioned carboxylic acid mixture was esterified with a hydrogenate-composition reaction product solution containing 50% by volume, or more, of 1,6-hexanediol.

The resultant esterification product contained 3.1% by weight of 1,6-hexanediol, 1.1% by weight of 1,5-pentanediol and 0.06% by weight of 1,4-butanediol, and had an acid value (AV) of 0.8 mg-KOH/g and a saponification value (SV) of 343 mg-KOH/g.

The above-mentioned hydrogenate-decomposition reaction product mixture liquid was prepared in accordance with the method as disclosed in Example 1 of Japanese Unexamined Patent Publication (Kokai) No. 3-115237, and contained 61.6% by weight of 1,6-hexanediol, 8.5% by weight of 1,5-pentanediol and 0.8% by weight of 1,4-butanediol.

The analysis of the reaction products were carried out by the same method as described in the following examples.

The above-mentioned esterification product is referred to as an adipic acid-1,6-hexanediol esterification product hereinafter.

EXAMPLE 1

Preparation of a Catalyst

A catalyst-preparation glass vessel having a capacity of 2 liters was charged with 250 ml of an aqueous solution of 14.5% by weight of ammonium carbonate. To the ammonium carbonate solution, an aqueous solution of 0.157 mole of copper nitrate and 0.125 mole of zinc nitrate in 250 ml of water was added dropwise over a time span of 30 minutes, while stirring the mixture and maintaining the pH of the mixture at 6.5 and the temperature of the mixture at 80° to 85° C. After the dropwise addition was completed, the resultant mixture was allowed to cool while stirring. During the cooling, the pH of the mixture increased to 8.2.

The resultant precipitate was collected by filtering, rinsed with water, dried at a temperature of 120° C. and screened through a 70 mesh sieve.

The resultant basic copper and zinc carbonate mixture (a first precursor of the catalytic material (A)) in an amount of 4 g was placed in a glass boat-shaped container and the container was placed in a glass tube having an inside diameter of 25 mm.

A reduction gas comprising 2% by volume of hydrogen diluted with nitrogen gas flowed through the glass tube at a flow rate of 12 liters/hr, while heating at a temperature of 110° C. for one hour, 170° C. for one hour and then 270° C. for one hour, then the concentration of hydrogen in the reduction gas was increased to 30% by volume and the reduction gas flowed through the glass tube at a temperature of 270° C. for one hour. After the hydrogen reduction was completed, the resultant reduction product (a second precursor of catalytic material (A)) was cooled to room temperature.

Next, an oxidation gas containing 0.1% by volume of oxygen diluted by nitrogen flowed through the glass tube at a flow rate of 36 liters/hr at room temperature for 10 hours and then the concentration of oxygen in the oxidation gas was gradually increased while flowing it through the glass tube. When the oxygen concentration reached 20% by volume, the oxidation procedure was completed.

The resultant catalyst had an atomic ratio of copper to zinc (Cu/Zn) of 1:1 and a degree of oxidation of copper was 19.1%.

The atomic ratio of Cu/Zn of the catalyst was determined by dissolving the catalyst in hydrochloric acid and subjecting it to atomic-absorption spectroscopic analysis. The degree of oxidation of copper was determined by measuring the change in weight of the catalyst while heating the catalyst to a temperature of 500° C. by a thermogravimetric analyzer (trademark: TGA 50, made by Shimazu Seisakusho) using a carrier gas consisting of hydrogen gas. The decrease in weight of the catalyst was derived from partial oxidation of copper. The degree of partial oxidation of copper was calculated based on the provision that copper and oxygen are bonded to each other in an atomic ratio of Cu/O of 1:1.

Hydrogenate-decomposition of the Esterification Product of Carboxylic Acid Mixture The adipic acid-1,6-hexanediol esterification product in an amount of 350 g was placed together with 3.5 g of the catalyst in a stainless steel autoclave with a capacity of 500 ml, and hydrogen gas was blown into the autoclave at a temperature of 25° C. under pressure. After the inside pressure of the autoclave reached 180 kg/cm$^2$G, the temperature of the charge in the autoclave was increased to 280° C., while stirring the charge. Then, the esterification product was hydrogenate-decomposed at a constant reaction temperature of 280° C. for 5 hours while controlling the hydrogen gas pressure in the autoclave to a level of 280 kg/cm$^2$G by adding hydrogen gas to the autoclave.

After the reaction was completed, 350 ml of the resultant reaction product mixture liquid was fed into a pressure filtering device having a capacity of 500 ml, equipped with a 10 μm membrane filter with an effective diameter of 45 mm heated to a temperature of 55° C. and filtered under a pressure of 1.0 kg/cm$^2$G applied by a nitrogen gas.

The filtering time of the mixture liquid was determined by measuring, after a first fraction of the mixture liquid in an amount of 50 ml passed through the filter, the time necessary to filter the next 50 ml, through the filter, by using a stopwatch.

The diol compounds, for example, 1,6-hexanediol, produced by the hydrogenate-decomposition reaction were identified by analyzing the filtrate obtained from the above-mentioned filtering procedure by gas chromatography.

The filtering time was 0.2 minute which was excellent and the resultant diol compounds included 57.5% by weight of 1,6-hexanediol, 9.5% by weight of 1,5-pentanediol and 0.8% by weight of 1,4-butanediol.

EXAMPLE 2

Diol compounds were produced from the adipic acid-1,6-hexanediol esterification product by the same procedure as in Example 1 with the following exceptions.

The adipic acid-1,6-hexanediol esterification product in an amount of 100 g was placed together with 2 g of the catalyst in a stainless steel autoclave with a capacity of 500 ml and hydrogen gas was blown into the autoclave, at a temperature of 25° C., under pressure. After the inside pressure of the autoclave reached 180 kg/cm²G, the temperature of the charge in the autoclave was increased to 280° C., while stirring the charge. Then, the esterification product was hydrogenate-decomposed at a constant reaction temperature of 280° C. for 3 hours. The hydrogen gas pressure in the autoclave was 250 kg/cm²G at the start of the reaction.

In this example and the following Example 3 and Comparative Examples 1 to 3, the catalytic activity of the catalyst was represented by a hydrogen absorption rate calculated from the time necessary to decrease the hydrogen pressure in the autoclave from 240 kg/cm²G to 210 kg/cm²G, instead of the rate or change of the esterifying alcohols in the reaction mixture.

The catalyst-preparation conditions and the results are shown in Table 1.

COMPARATIVE EXAMPLE 1

The same hydrogenate-decomposition and analysis procedures as in Example 2 were carried out except that the copper and zinc-containing catalyst of Example 1 was replaced by 2 g of a conventional copper and chromium-containing catalyst (trademark: N203, made by Nikki Kagaku K.K.).

The hydrogen absorption rate was 0.863 mole/hr and the filtering time was 3.2 minutes as shown in Table 1.

EXAMPLE 3

Preparation of Catalyst

A copper and zinc-containing catalyst was prepared by the same procedure as in Example 1, except that the aqueous ammonium carbonate solution was replaced by 460 ml of an aqueous solution of 10% by weight of sodium carbonate, and the aqueous copper nitrate and zinc nitrate solution was replaced by an aqueous solution of 0.12 mole of copper nitrate and 0.28 mole of zinc nitrate in 400 ml of water.

Hydrogenate-decomposition of Esterification Product

The same hydrogenate-decomposition procedure as in Example 2 was carried out except that the above-mentioned catalyst was employed in an amount of 2 g.

The catalyst-preparation conditions and results are shown in Table 1.

TABLE 1

| | Preparation of catalyst | | | | | Properties of catalyst | | Hydrogenate-decomposition results | |
|---|---|---|---|---|---|---|---|---|---|
| | | | | pH | | | Oxidation | Hydrogen | |
| | Atomic | Mixing | | | | Atomic | degree of | absorption | |
| Example No. | ratio Cu/Zn | temperature (°C.) | Precipitant | Immediately after mixing | After aging | ratio Cu/Zn | copper (%) | rate (mole/hr) | Filtering (min) |
| Example 2 | 5/5 | 80–85 | Ammonium carbonate | 6.5 | 8.2 | 5/5 | 19.1 | 1.410 | 1.2 |
| Comparative Example 1 | | | (*)₁ | | | — | — | 0.863 | 3.2 |
| Example 3 | 3/7 | 80–85 | Sodium carbonate | 6.5 | 8.2 | 3/7 | 48.5 | 2.250 | 6.0 |

Note: (*)₁ . . . Conventional copper and chromium-containing catalyst Trademark: N203, made by Nikki Kagaku K.K.

EXAMPLE 4

Preparation of a Catalyst

Water in an amount of 200 ml was placed in a glass container (catalyst-preparation vessel) and heated to 80° C., and an aqueous solution of 0.25 mole of copper nitrate and 0.25 mole of zinc nitrate in 500 ml and an aqueous solution of 10% by weight of sodium carbonate were simultaneously added dropwise to the heated water while stirring the mixture. The dropping rate of the aqueous sodium carbonate solution was adjusted to 8 g/min, and the dropping rate of the aqueous copper nitrate and zinc nitrate solution was controlled to such an extent that the pH of the mixed solution was maintained at 8.0.

When the dropped amount of the aqueous sodium carbonate solution reached 650 ml, the dropping operation of both the aqueous solutions were completed, and the resultant mixture was further stirred at a temperature of 80° C. for 1.5 hours to age the precipitate. During the aging, the pH of the mixture increased to 8.8.

The resultant precipitate (basic copper and zinc carbonate mixture) was filtered, rinsed with water, dried at a temperature of 120° C. and then screened through a 70 mesh sieve.

The dried precipitate was subjected to the same hydrogen reduction and partial oxidation procedures as in Example 1, to prepare a catalyst.

Hydrogenate-decomposition

The adipic acid-1,6-hexanediol esterification product was hydrogenate-decomposed by the same procedures as in Example 2 except that the above-mentioned catalyst was employed in an amount of 2 g.

The catalyst-preparation conditions and the results are shown in Table 2.

COMPARATIVE EXAMPLE 2

The same catalyst-preparation, hydrogenate-decomposition and analysis procedures as in Example 4 were carried out except that the precipitate comprising the basic copper and zinc carbonate mixture was calcined in air at a temperature of 450° C. for one hour and then subjected to the hydrogen reduction and the partial oxidation.

The catalyst preparation conditions and the results are shown in Table 2.

EXAMPLE 5

The same catalyst-preparation, hydrogenate-decomposition and analysis procedures as in Example 4 were carried out except that in the mixing step of the catalyst preparation, the pH of the mixture was maintained at 6.5, and after the dropping of the aqueous sodium carbonate solution was completed, the pH of the mixture increased to 7.6 during the aging.

The catalyst-preparation conditions and the results are shown in Table 2.

EXAMPLE 6

The same catalyst-preparation, hydrogenate-decomposition and analysis procedures as in Example 4 were carried out except that in the mixing step of the catalyst preparation, the pH of the mixture was maintained at a level of 9.0, and after the completion of the dropping of the aqueous sodium carbonate solution, the pH of the mixture increased to 9.3 during the aging.

The catalyst preparation conditions and the results are shown in Table 2.

EXAMPLE 7

The same catalyst-preparation, hydrogenate-decomposition and analysis procedures as in Example 4 were carried out except that the aqueous copper nitrate and zinc nitrate solution was prepared by dissolving 0.10 mole of copper nitrate and 0.40 mole of zinc nitrate in 500 ml of water, and after the completion of the dropping of the aqueous sodium carbonate solution, the pH of the mixture increased to 8.6 during the aging.

The catalyst-preparation conditions, and the reaction results are shown in Table 2.

EXAMPLE 8

The same catalyst-preparation, hydrogenate-decomposition and analysis procedures as in Example 4 were carried out except that the aqueous copper nitrate and zinc nitrate solution was prepared by dissolving 0.15 mole of copper nitrate and 0.35 mole of zinc nitrate in 500 ml of water, and after the completion of the dropping of the aqueous sodium carbonate solution, the pH of the mixture raised increased to 8.5 during the aging.

The catalyst-preparation conditions and the reaction results are shown in Table 2.

EXAMPLE 9

The same catalyst-preparation, hydrogenate-decomposition and analysis procedures as in Example 4 were carried out except that the aqueous copper nitrate and zinc nitrate solution was prepared by dissolving 0.20 mole of copper nitrate and 0.30 mole of zinc nitrate in 500 ml of water, and after the completion of the dropping of the aqueous sodium carbonate solution, the pH of the mixture increased to 8.7 during the aging.

The catalyst-preparation conditions and the reaction results are shown in Table 2.

EXAMPLE 10

The same catalyst-preparation, hydrogenate-decomposition and analysis procedures as in Example 4 were carried out except that the aqueous copper nitrate and zinc nitrate solution was prepared by dissolving 0.30 mole of copper nitrate and 0.20 mole of zinc nitrate in 500 ml of water, and after the completion of the dropping of the aqueous sodium carbonate solution, the pH of the mixture increased to 8.9 during the aging.

The catalyst-preparation conditions and the reaction results are shown in Table 2.

EXAMPLE 11

The same catalyst-preparation, hydrogenate-decomposition and analysis procedures as in Example 4 were carried out except that in the mixing step of the catalyst preparation, the temperature of the mixture was maintained at 60° C., and after the dropping of the aqueous sodium carbonate solution was completed, the pH of the mixture increased to 9.5 during the aging.

The catalyst preparation conditions and reaction results are shown in Table 2.

EXAMPLE 12

The same catalyst-preparation, hydrogenate-decomposition and analysis procedures as in Example 4 were carried out except that in the mixing step of the catalyst preparation, the mixing was carried out at a refluxing temperature of the mixture, and after the dropping of the aqueous sodium carbonate solution was completed, the pH of the mixture increased to 9.5 during the aging.

The catalyst preparation conditions and the reaction results are shown in Table 2.

EXAMPLE 13

The same catalyst-preparation, hydrogenate-decomposition and analysis procedures as in Example 4 were carried out except that the aqueous copper nitrate and zinc nitrate solution was replaced by an aqueous solution of 0.025 mole of copper sulfate and 0.25 mole of zinc sulfate in 500 ml of water, and after the completion of the dropping of the aqueous sodium carbonate solution, the pH of the mixture increased to 8.8 during the aging.

The catalyst-preparation conditions and the reaction results are shown in Table 2.

TABLE 2

| Example No. | Preparation of catalyst | | | | | Properties of catalyst | | Hydrogenate-decomposition results | |
|---|---|---|---|---|---|---|---|---|---|
| | Atomic ratio Cu/Zn | Mixing temperature (°C.) | Precipitant | pH Immediately after mixing | pH After aging | Atomic ratio Cu/Zn | Oxidation degree of copper (%) | Hydrogen absorption rate (mole/hr) | Filtering time (min) |
| Example 4 Comparative | 5/5 | 80 | Na₂CO₃ | 8.0 | 8.8 | 5/5 | 40.7 | 2.250 | 2.0 |
| Example 2 Example | 5/5 | 80 | Na₂CO₃ | 8.0 | 8.8 | 5/5 | 9.0 | 0.787 | 4.4 |
| 5 | 5/5 | 80 | Na₂CO₃ | 6.5 | 7.6 | 5/5 | 37.1 | 1.610 | 1.3 |
| 6 | 5/5 | 80 | Na₂CO₃ | 9.0 | 9.3 | 5/5 | 35.0 | 1.875 | 1.9 |
| 7 | 2/8 | 80 | Na₂CO₃ | 8.0 | 8.6 | 2/8 | 72.6 | 1.733 | 3.0 |
| 8 | 3/7 | 80 | Na₂CO₃ | 8.0 | 8.5 | 3/7 | 53.2 | 2.498 | 5.3 |
| 9 | 4/6 | 80 | Na₂CO₃ | 8.0 | 8.7 | 4/6 | 45.5 | 2.048 | 3.1 |
| 10 | 6/4 | 80 | Na₂CO₃ | 8.0 | 8.9 | 6/4 | 27.7 | 1.733 | 2.6 |
| 11 | 5/5 | 60 | Na₂CO₃ | 8.0 | 8.8 | 5/5 | 35.8 | 1.875 | 1.9 |
| 12 | 5/5 | reflux | Na₂CO₃ | 8.8 | 9.5 | 5/5 | 40.8 | 1.815 | 3.8 |
| 13 | 5/5 | 80 | Na₂CO₃ | 8.0 | 8.8 | 5/5 | 36.6 | 1.428 | 2.5 |

EXAMPLE 14

The same catalyst-preparation, hydrogenate-decomposition and analysis procedures as in Example 4 were carried out with the following exceptions.

Preparation of a Catalyst

The same basic copper and zinc carbonate mixture as in Example 4 was hydrogen-reduced with a reduction gas comprising 2% by volume of hydrogen diluted by nitrogen gas in such a manner that the reduction gas flowed at a rate of 12 liters/hr through the glass tube, the temperature of the reduction reaction system in the glass tube was increased at a rate of 30 ° C./hr to a level of 280° C., and the reaction temperature was maintained at this level for one hour. After the reduction reaction with hydrogen was completed, the resultant reduction product was cooled to room temperature by passing nitrogen gas through the glass tube.

Hydrogenate-decomposition

The above-mentioned catalyst was employed in an amount of 2 g.

The catalyst preparation conditions and the reaction results are shown in Table 3.

EXAMPLES 15 to 19

In each of Examples 15 to 19, the same catalyst-preparation, hydrogenate-decomposition and analysis procedures as in Example 14 were carried out except that the hydrogen reduction of the basic copper and zinc carbonate mixture was carried out in the hydrogen concentration of the reduction gas, at the temperature-increase rate and the reduction temperature shown in Table 3.

The catalyst-preparation conditions and the results are shown in Table 3.

TABLE 3

| Example No. | Preparation of catalyst | | | Properties of catalyst | | Hydrogenate-decomposition results | |
|---|---|---|---|---|---|---|---|
| | Reduction temperature (°C.) | Temperature-increase rate (°C./hr) | H₂-concentration (% by volume) | Atomic ratio Cu/Zn | Oxidation degree of copper (%) | Hydrogen absorption rate (mole/hr) | Filtering time (min) |
| Example | | | | | | | |
| 14 | 280 | 30 | 2 | 5/5 | 26.3 | 1.410 | 1.2 |
| 15 | 275 | 60 | 2 | 5/5 | 19.4 | 0.983 | 1.7 |
| 16 | 275 | 30 | 2 | 5/5 | 22.4 | 1.320 | 1.8 |
| 17 | 275 | 15 | 2 | 5/5 | 28.3 | 1.725 | 1.8 |
| 18 | 275 | 30 | 10 | 5/5 | 28.4 | 1.733 | 1.6 |
| 19 | 275 | 30 | 30 | 5/5 | 28.2 | 1.718 | 1.7 |

EXAMPLE 20

The same catalyst-preparation, hydrogenate-decomposition and analysis procedures as in Example 4 were carried out with the following exceptions.

Preparation of a Catalyst

The same basic copper and zinc carbonate mixture as in Example 4 was hydrogen-reduced with a reduction gas comprising 2% by volume of hydrogen diluted by nitrogen gas in such a manner that the reduction gas flowed at a rate of 12 liters/hr through the glass tube, the temperature of the reduction reaction system in the glass tube was increased at a rate of 30° C./hr to a level of 350° C., and the reaction temperature was maintained at this level for one hour. After the reduction reaction with hydrogen was completed, the resultant reduction product was cooled to room temperature by passing nitrogen gas through the glass tube.

Hydrogenate-decomposition

The above-mentioned catalyst was employed in an amount of 2 g.

The catalyst preparation conditions and the reaction results are shown in Table 4.

EXAMPLES 21 to 25

In each of Examples 21 to 25, the same catalyst-preparation, hydrogenate-decomposition and analysis procedures as in Example 14 were carried out except that the hydrogen reduction of the basic copper and zinc carbonate mixture was carried out in the hydrogen concentration of the reduction gas, at the temperature-increase rate and the reduction temperature shown in Table 4.

The catalyst-preparation conditions and the results are shown in Table 4.

at 6.5 and the temperature of the mixture at 80° to 85° C. After the dropping was completed, the resultant mixture was allowed to cool while being stirred. During the cooling, the pH of the mixture increased to 8.2.

The resultant precipitate was collected by filtering, rinsed with water, dried at a temperature of 120° C. and screened through a 70 mesh sieve.

The resultant basic copper and zinc carbonate mixture (a precursor of the catalytic material (B)) was calcined at a temperature of 450° C. for one hour to provide a catalyst.

The resultant catalyst had an atomic ratio of copper to zinc (Cu/Zn) of 1:1.

The atomic ratio of Cu/Zn of the catalyst was determined by atomic-absorption spectroscopic analysis, as mentioned in Example 1.

Hydrogenate-decomposition of the Esterification Product of Carboxylic Acid Mixture The adipic acid-1,6-hexanediol esterification product in an amount of 350 g was placed together with 3.5 g of the catalyst in a stainless steel autoclave with a capacity of 500 ml, and hydrogen gas was blown into the autoclave at a temperature of 25° C. under pressure. After the inside pressure of the autoclave reached 180 kg/cm$^2$ the temperature of the charge in the autoclave was increased to 280° C., while the change was stirred. Then, the esterification product was hydrogenate-decomposed at a constant reaction temperature of 280° C. for 5 hours while controlling the hydrogen gas pressure in the autoclave at a level of 280 kg/cm$^2$G while supplementing hydrogen gas into the autoclave.

After the reaction was completed, 350 ml of the resultant reaction product mixture liquid was fed into a pressure filtering device having a capacity of 500 ml, equipped with a 10 μm membrane filter (effective diameter: 45 mm) and

TABLE 4

| | Preparation of catalyst | | | Properties of catalyst | | Hydrogenate-decomposition results | |
|---|---|---|---|---|---|---|---|
| Example No. | Reduction temperature (°C.) | Temperature-increase rate (°C./hr) | H$_2$-concentration (% by volume) | Atomic ratio Cu/Zn | Oxidation degree of copper (%) | Hydrogen absorption rate (mole/hr) | Filtering time (min) |
| Example | | | | | | | |
| 20 | 350 | 30 | 2 | 5/5 | 22.2 | 1.410 | 2.8 |
| 21 | 275 | 30 | 10 | 5/5 | 40.3 | 1.875 | 2.6 |
| 22 | 250 | 30 | 10 | 5/5 | 36.0 | 1.950 | 2.1 |
| 23 | 225 | 30 | 10 | 5/5 | 47.5 | 2.250 | 2.7 |
| 24 | 200 | 30 | 10 | 5/5 | 52.7 | 2.625 | 3.0 |
| 25 | 175 | 30 | 50 | 5/5 | 56.3 | 2.175 | 4.9 |

EXAMPLE 26

Preparation of a Catalyst

A catalyst-preparation glass vessel having a capacity of 2 liters was charged with 250 ml of an aqueous solution of 14.5% by weight of ammonium carbonate. To the ammonium carbonate solution, an aqueous solution of 0.157 mole of copper nitrate and 0.125 mole of zinc nitrate in 250 ml of water was added dropwise over a time of 30 minutes, while stirring the mixture and maintaining the pH of the mixture heated at a temperature of 55° C., and filtered under pressure of 1.0 kg/cm$^2$G applied by a nitrogen gas.

The filtering time of the mixture liquid was determined by measuring, after a first fraction of the mixture liquid in an amount of 50 ml passed through the filter, the time necessary to filter the following 50 ml through the filter, by using a stopwatch.

The diol compounds, for example, 1,6-hexanediol, produced by the hydrogenate-decomposition reaction were identified by analyzing the filtrate obtained from the above-mentioned filtering procedure by gas chromatography.

The filtering time was 0.5 minutes which was excellent and the resultant diol compounds included 50.3% by weight of 1,6-hexanediol, 10.2% by weight of 1,5-pentanediol and 0.7% by weight of 1,4-butanediol.

EXAMPLE 27

Diol compounds were produced from the adipic acid-1,6-hexanediol esterification product by the same procedures as in Example 26 with the following exceptions.

The adipic acid-1,6-hexanediol esterification product in an amount of 100 g was placed together with 2 g of the catalyst in a stainless steel autoclave with a capacity of 500 ml, and hydrogen gas was blown into the autoclave at a temperature of 25° C. under pressure. After the inside pressure of the autoclave reached 180 kg/cm$^2$G, the temperature of the charge in the autoclave was increased to 280° C. while the charge was stirred Then, the esterification product was hydrogenate-decomposed at a constant reaction temperature of 280° C. for 3 hours. The hydrogen gas pressure in the autoclave was 250 kg/cm$^2$G at the start of the reaction.

In this example and the following Examples 28 to 35 and Comparative Examples 5 to 11, the catalytic activity of the catalyst was represented by a hydrogen absorption rate calculated from the time necessary to decrease the hydrogen pressure in the autoclave from 240 kg/cm$^2$G to 210 kg/cm$^2$G, instead of the rate of change of the esterifying alcohols in the reaction mixture.

The catalyst-preparation conditions and the results are shown in Table 5.

EXAMPLE 28

The same catalyst-preparation, hydrogenate-decomposition and analysis procedures as in Example 27 were carried out except that the aqueous ammonium carbonate solution was replaced by 250 ml of an aqueous solution of 17.8% by weight of ammonium hydrogen carbonate, the aqueous copper nitrate and zinc nitrate solution was prepared by dissolving 0.126 mole of copper nitrate and 0.10 mole of zinc nitrate in 200 ml of water, and the pH of the mixture was maintained at a level of 6.7.

Also, during cooling, the pH of the mixture in the catalyst preparation vessel increased to 8.1.

The catalyst preparation conditions and the results are shown in Table 5.

EXAMPLE 29

Preparation of a Catalyst

Water in an amount of 200 ml was placed in a glass container (catalyst-preparation vessel) and heated to 80° C., and an aqueous solution of 0.25 mole of copper nitrate and 0.25 mole of zinc nitrate in 500 ml and an aqueous solution of 10% by weight of sodium carbonate were simultaneously added dropwise to the hot water while stirring the mixture. The dropping rate of the aqueous sodium carbonate solution was adjusted to 8 g/min, and the dropping rate of the aqueous copper nitrate and zinc nitrate solution was controlled so that the pH of the mixed solution was maintained at 8.0.

When the dropped amount of the aqueous sodium carbonate solution reached 650 ml, the dropping operation of both the aqueous solutions were completed, and the resultant mixture was further stirred at a temperature of 80° C. for 1.5 hours to age the precipitate. During the aging, the pH of the mixture increased to 8.8.

The resultant precipitate (basic copper and zinc carbonate mixture) was filtered, rinsed with water, dried at a temperature of 120° C. and then screened through a 70 mesh sieve.

The dried precipitate was calcined in air at a temperature of 450° C. for one hour.

Hydrogenate-decomposition

The adipic acid-1,6-hexanediol esterification product was hydrogenate-decomposed by the same procedures as in Example 27 except that the above-mentioned catalyst was employed in an amount of 2 g.

The catalyst-preparation conditions and the results are shown in Table 5.

EXAMPLE 30

The same catalyst-preparation, hydrogenate-decomposition and analysis procedures as in Example 29 were carried out except that in the mixing step of the catalyst preparation, the temperature of the mixture in the catalyst preparation vessel was maintained at a level of 60° C., and after the dropping of the aqueous sodium carbonate solution was completed, the pH of the mixture increased to 8.8 during the aging.

The catalyst preparation conditions and reaction results are shown in Table 5.

COMPARATIVE EXAMPLE 3

The same catalyst-preparation, hydrogenate-decomposition and analysis procedures as in Example 29 were carried out except that in the mixing step of the catalyst preparation, the temperature of the mixture in the catalyst preparation vessel was maintained at 40° C., and after the dropping of the aqueous sodium carbonate solution was completed, the pH of the mixture increased to 8.5 during the aging.

The catalyst preparation conditions and reaction results are shown in Table 5.

COMPARATIVE EXAMPLE 4

The same catalyst-preparation, hydrogenate-decomposition and analysis procedures as in Example 29 were carried out except that in the mixing step of the catalyst preparation, the mixing was carried out at a refluxing temperature of the mixture, and after the dropping of the aqueous sodium carbonate solution was completed, the pH of the mixture increased to 9.5 during the aging.

The catalyst preparation conditions and the reaction results are shown in Table 5.

TABLE 5

| | Preparation of catalyst | | | | | | Catalyst | Hydrogenate-decomposition results | |
|---|---|---|---|---|---|---|---|---|---|
| | Atomic | Mixing | | pH | | Calcining | Atomic | Hydrogen | |
| Example No. | ratio Cu/Zn | temperature (°C.) | Precipitant | Immediately after mixing | After aging | temperature (°C.) | ratio Cu/Zn | absorption rate (mole/hr) | Filtering time (min) |
| Example | | | | | | | | | |
| 27 | 5/5 | 80 | Ammonium carbonate | 6.5 | 8.2 | 450 | 5/5 | 0.645 | 2.1 |
| 28 | 5/5 | 80 | Ammonium hydrogen carbonate | 6.7 | 8.1 | 450 | 5/5 | 0.607 | 5.0 |
| 29 | 5/5 | 80 | $Na_2CO_3$ | 8.0 | 8.8 | 450 | 5/5 | 0.713 | 1.7 |
| 30 | 5/5 | 60 | " | 8.0 | 8.8 | 450 | 5/5 | 0.645 | 6.8 |
| Comparative Example | | | | | | | | | |
| 3 | 5/5 | 40 | " | 8.0 | 8.5 | 450 | 5/5 | 0.593 | 61.1 |
| 4 | 5/5 | reflux | " | 8.8 | 9.5 | 450 | 5/5 | 0.900 | 43.1 |

EXAMPLE 31

The same catalyst-preparation, hydrogenate-decomposition and analysis procedures as in Example 29 were carried out except that in the mixing step of the catalyst preparation, the pH of the mixture was maintained at 6.5, and after the dropping of the aqueous sodium carbonate solution was completed, the pH of the mixture increased to 7.6 during the aging.

The catalyst-preparation conditions and the results are shown in Table 6.

EXAMPLE 32

The same catalyst-preparation, hydrogenate-decomposition and analysis procedures as in Example 29 were carried out except that in the mixing step of the catalyst preparation, the pH of the mixture was maintained at 9.0, and after the completion of the dropping of the aqueous sodium carbonate solution, the pH of the mixture increased to 9.3 during the aging.

The catalyst preparation conditions and the results are shown in Table 6.

COMPARATIVE EXAMPLE 5

The same catalyst-preparation, hydrogenate-decomposition and analysis procedures as in Example 29 were carried out except that in the mixing step of the catalyst preparation, the pH of the mixture in the catalyst preparation vessel was maintained at a level of 9.5.

No basic copper and zinc carbonate mixture precipitate was obtained.

COMPARATIVE EXAMPLE 6

A copper and zinc-containing catalyst was prepared by the same procedures as in Example 29, except that 460 ml of an aqueous solution of 10% by weight of sodium carbonate was placed in a 2 liter glass container (catalyst preparation vessel) and maintained at a temperature of 80° to 85° C., and an aqueous solution of 0.12 mole of copper nitrate and 0.28 mole of zinc nitrate in 400 ml of water was added dropwise to the aqueous sodium carbonate solution. At the start of the dropwise addition, the pH of the aqueous sodium carbonate solution was 11.0.

After the dropping of the aqueous copper nitrate and zinc nitrate solution was completed, the pH of the mixture in the catalyst preparation vessel was 7.3, and the mixture was aged while maintaining the pH thereof at this level.

The catalyst preparation conditions and the reaction results are shown in Table 6.

COMPARATIVE EXAMPLE 7

The same catalyst-preparation, hydrogenate-decomposition and analysis procedures as in Example 29 were carried out except that the aqueous copper nitrate and zinc nitrate solution was prepared by dissolving 0.25 mole of copper nitrate and 0.25 mole of zinc nitrate in 500 ml of water, placed in a 2 liter glass container (catalyst preparation vessel) and heated to 80° to 85° C., and 470 ml of an aqueous 10% by weight sodium carbonate solution were added dropwise.

At the start of the addition, the pH of the aqueous copper nitrate and zinc nitrate solution was 2.0.

After the completion of the dropping of the aqueous sodium carbonate solution, the pH of the mixture in the catalyst preparation vessel was 6.9. The mixture was aged at this pH.

The catalyst-preparation conditions and the reaction results are shown in Table 6.

EXAMPLE 33

The same catalyst-preparation, hydrogenate-decomposition and analysis procedures as in Example 29 were carried out except that the aqueous copper nitrate and zinc nitrate solution was prepared by dissolving 0.20 mole of copper nitrate and 0.30 mole of zinc nitrate in 500 ml of water, and after the completion of the dropping of the aqueous sodium carbonate solution, the pH of the mixture increased to 8.7 during the aging.

The catalyst-preparation conditions and the reaction results are shown in Table 6.

EXAMPLE 34

The same catalyst-preparation, hydrogenate-decomposition and analysis procedures as in Example 29 were carried out except that the aqueous copper nitrate and zinc nitrate solution was prepared by dissolving 0.25 mole of copper nitrate and 0.25 mole of zinc nitrate in 500 ml of water, and after the completion of the dropping of the aqueous sodium carbonate solution, the pH of the mixture increased to 8.8 during the aging.

The catalyst-preparation conditions and the reaction results are shown in Table 6.

EXAMPLE 35

The same catalyst-preparation, hydrogenate-decomposition and analysis procedures as in Example 29 were carried out except that the aqueous copper nitrate and zinc nitrate solution was prepared by dissolving 0.30 mole of copper nitrate and 0.20 mole of zinc nitrate in 500 ml of water, and after the completion of the dropping of the aqueous sodium carbonate solution, the pH of the mixture increased to 8.9 during the aging.

The catalyst-preparation conditions and the reaction results are shown in Table 6.

COMPARATIVE EXAMPLE 8

The same catalyst-preparation, hydrogenate-decomposition and analysis procedures as in Example 29 were carried out except that the aqueous copper nitrate and zinc nitrate solution was prepared by dissolving 0.15 mole of copper nitrate and 0.35 mole of zinc nitrate in 500 ml of water, and after the completion of the dropping of the aqueous sodium carbonate solution, the pH of the mixture increased to 8.5 during the aging.

The catalyst-preparation conditions and the reaction results are shown in Table 6.

COMPARATIVE EXAMPLE 9

The same catalyst-preparation, hydrogenate-decomposition and analysis procedures as in Example 29 were carried out except that the aqueous copper nitrate and zinc nitrate solution was prepared by dissolving 0.40 mole of copper nitrate and 0.10 mole of zinc nitrate in 500 ml of water, and after the completion of the dropping of the aqueous sodium carbonate solution, the pH of the mixture increased to 9.0 during the aging.

The catalyst-preparation conditions and the reaction results are shown in Table 6.

TABLE 6

| | Preparation of catalyst | | | | | | Catalyst | Hydrogenate-decomposition results | |
| --- | --- | --- | --- | --- | --- | --- | --- | --- | --- |
| | Atomic | Mixing | | pH | | Calcining | Atomic | Hydrogen | |
| Example No. | ratio Cu/Zn | temperature (°C.) | Precipitant | Immediately after mixing | After aging | temperature (°C.) | ratio Cu/Zn | absorption rate (mole/hr) | Filtering time (min) |
| Example | | | | | | | | | |
| 31 | 5/5 | 80 | Na$_2$CO$_3$ | 6.5 | 7.6 | 450 | 5/5 | 0.670 | 1.5 |
| 32 | 5/5 | 80 | " | 9.0 | 9.3 | 450 | 5/5 | 0.593 | 2.4 |
| Comparative Example | | | | | | | | | |
| 5 | 5/5 | 80 | " | 9.5 | — | — | — | — | — |
| 6 | 3/7 | 80 | " | 11.0 | 7.3 | 450 | 3/7 | 0.645 | 94.9 |
| 7 | 5/5 | 80 | " | 2.0 | 6.9 | 450 | 5/5 | 0.248 | 24.0 |
| Example | | | | | | | | | |
| 33 | 4/6 | 80 | " | 8.0 | 8.7 | 450 | 4/6 | 0.660 | 4.9 |
| 34 | 5/5 | 80 | " | 8.0 | 8.8 | 450 | 5/5 | 0.627 | 2.3 |
| 35 | 6/4 | 80 | " | 8.0 | 8.9 | 450 | 6/4 | 0.833 | 9.5 |
| Comparative Example | | | | | | | | | |
| 8 | 3/7 | 80 | " | 8.0 | 8.5 | 450 | 3/7 | 0.473 | 12.6 |
| 9 | 8/2 | 80 | " | 8.0 | 9.0 | 450 | 8/2 | 0.510 | 12.1 |

EXAMPLE 36

The same catalyst-preparation, hydrogenate-decomposition and analysis procedures as in Example 29 were carried out except that the aqueous copper nitrate and zinc nitrate solution was replaced by an aqueous solution of 0.025 mole of copper sulfate and 0.25 mole of zinc sulfate in 500 mole of water, and after the completion of the dropping of the aqueous sodium carbonate solution, the pH of the mixture increased to 8.7 during the aging. Also, the calcining step was carried out at a temperature of 440° C.

25

The catalyst-preparation conditions and the reaction results are shown in Table 7.

EXAMPLE 37

The same catalyst-preparation, hydrogenate-decomposition and analysis procedures as in Example 36 were carried out except that the calcining step was carried out at a temperature of 300° C. Also, after the completion of the dropwise addition of the aqueous sodium carbonate solution, the pH of the mixture increased to 8.7.

The catalyst preparation conditions and the results are shown in Table 7.

COMPARATIVE EXAMPLE 10

The same catalyst-preparation, hydrogenate-decomposition and analysis procedures as in Example 36 were carried out except that the calcining step was carried out at a temperature of 280° C. Also, after the completion of the dropwise addition of the aqueous sodium carbonate solution, the pH of the mixture increased to 8.7.

The catalyst preparation conditions and the results are shown in Table 7.

COMPARATIVE EXAMPLE 11

The same catalyst-preparation, hydrogenate-decomposition and analysis procedures as in Example 36 were carried out except that the calcining step was carried out at a temperature of 500° C. Also, after the completion of the dropwise addition of the aqueous sodium carbonate solution, the pH of the mixture increased to 8.7.

The catalyst preparation conditions and the results are shown in Table 7.

26 with 2 g of the same catalyst as in Example 23 was placed in a SUS autoclave having a capacity of 500 ml. Into the autoclave, hydrogen gas was introduced at a temperature of 25° C. under a pressure of 180 $kg/cm^2G$. Then, the reaction mixture in the autoclave was heated to a temperature of 240° C. while it was stirred. Thereafter, the reaction mixture was subjected to a hydrogenate-decomposition reaction under a hydrogen pressure of 250 $kg/cm^2G$ at the start of the reaction for one hour.

The hydrogen-absorption rate was 1.50 moles/hr and the filtering time was 0.4 minute. As a result of analysis, it was found that the resultant reaction product mixture contained 79.1% by weight of lauryl alcohol, 18.5% by weight of ethyl alcohol, and 1.4% by weight of ethyl laurate.

The hydrogenate-decomposition conditions and the results are shown in Table 8.

COMPARATIVE EXAMPLE 14

The same procedures as in Example 38 were carried out except that the copper and zinc-containing catalyst of Example 38 was replaced by 2 g of a conventional copper-chromium-containing catalyst (trademark: N203, made by Nikki Kagaku K.K.), the hydrogenate-decomposition reaction was carried out at a temperature of 260° C., under a hydrogen pressure, at the start of the reaction, of 260 $kg/cm^2$ for 2 hours.

The hydrogen absorption rate was 0.45 mole/hr and the filtering time was 0.7 minute.

As a result of the analysis, it was found that the resultant reaction product mixture contained 79.3% by weight of lauryl alcohol, 18.3% by weight of ethyl alcohol and 1.1% by weight of ethyl laurate.

The hydrogenate-decomposition conditions and the results are shown in Table 8.

TABLE 7

| | Item | | | | | | | | |
|---|---|---|---|---|---|---|---|---|---|
| | Preparation of catalyst | | | | | | Catalyst | Hydrogenate-decomposition results | |
| | Atomic | Mixing | | pH | | Calcining | Atomic | Hydrogen | |
| Example No. | ratio Cu/Zn | temperature (°C.) | Precipitant | Immediately after mixing | After aging | temperature (°C.) | ratio Cu/Zn | absorption rate (mole/hr) | Filtering time (min) |
| Example | | | | | | | | | |
| 36 | 5/5 | 80 | $Na_2CO_3$ | 8.0 | 8.7 | 440 | 5/5 | 0.828 | 2.9 |
| 37 | 5/5 | 80 | " | 8.0 | 8.7 | 300 | 5/5 | 1.539 | 5.1 |
| Comparative Example | | | | | | | | | |
| 10 | 5/5 | 80 | " | 8.0 | 8.7 | 280 | 5/5 | 0.773 | 42.4 |
| 11 | 5/5 | 80 | " | 8.0 | 8.7 | 500 | 5/5 | 0.414 | 6.2 |

EXAMPLE 38

The same procedures for the hydrogenate-decomposition of carboxylic acid ester and analysis as in Example 23 were carried out except that a mixture of 100 g of ethyl laurate

TABLE 8

| | Hydrogenate-decomposition conditions | | | Hydrogenate-decomposition results | |
|---|---|---|---|---|---|
| Example No. | Catalyst | Temperature (°C.) | Time (hr) | Hydrogen absorption rate (mole/hr) | Filtering time (min) |
| Example 38 | Cu—CuO—ZnO | 240 | 1 | 1.50 | 0.4 |
| Comparative Example 14 | CuO—Cr$_2$O$_3$ (*)$^2$ | 260 | 2 | 0.45 | 0.7 |

Note: (*)$^2$ ... Conventional copper-chromium catalyst (trademark: N2O3, made by Nikki Kagaku K.K.)

We claim:

1. A process for producing diol compounds comprising the steps of:

esterifying a carboxylic acid mixture collected from a reaction product mixture liquid obtained by a liquid phase oxidation reaction of cyclohexane, with an esterifying alcohol, and hydrogenate-decomposing the resultant esterification product with hydrogen, wherein the hydrogenate-decomposition of the esterification product with hydrogen is carried out in a liquid phase suspension bed in the presence of a catalyst comprising at least one member selected from the group consisting of:

(A) copper and zinc-containing catalytic material prepared by mixing an aqueous solution containing a water-soluble copper salt and a water-soluble zinc salt with an aqueous solution containing at least one member selected from the group consisting of alkali metal carbonates, ammonium carbonate, alkali metal hydrogen carbonates and ammonium hydrogen carbonate to provide a precipitate comprising a water-insoluble basic copper and zinc carbonate mixture, reducing the precipitate with hydrogen in a reduction gas containing the hydrogen at a temperature of 100° C. to 400° C. and bringing the resultant reduction product into contact with an oxygen-containing gas; and (B) copper and zinc-containing catalytic material prepared by mixing an aqueous solution containing a water-soluble copper salt and a water-soluble zinc salt with an aqueous solution containing at least one member selected from the group consisting of an alkali metal carbonate, ammonium carbonate, alkali metal hydrogen carbonate and ammonium hydrogen carbonate at a temperature of 60° to 95°C. at a pH of 6.5 to 9.0, to provide a precipitate comprising an aurichalcite type copper-zinc double salt ((Cu, Zn)$_5$(CO$_3$)$_2$)(OH)$_6$), and calcining the precipitate at a temperature of 300° C. to 450° C.

2. The process as claimed in claim 1, wherein, in the preparation of the copper and zinc-containing catalytic material (A), the water-soluble copper salt and the water-soluble zinc salt are employed in an atomic ratio Cu/Zn of 1:9 to 9:1.

3. The process as claimed in claim 1, wherein, in the preparation of the copper and zinc-containing catalytic material (A), the mixing procedure of the aqueous solution containing the water-soluble copper salt and the water-soluble zinc salt with the aqueous solution containing at least one member selected from the group consisting of alkali metal carbonates, ammonium carbonate, alkali metal hydrogen carbonates and ammonium hydrogen carbonate is carried out at a temperature of 50° C. to 95° C. and at a pH of 6.5 to 9.5.

4. The process as claimed in claim 1, wherein, in the preparation of the copper and zinc-containing catalytic material (A), the contact of the reduction product with the oxygen-containing gas is carried out at a temperature of 100° C. or less.

5. The process as claimed in claim 1, wherein the preparation of the copper and zinc-containing catalyst (A) is free from a calcining step at a temperature of 300° C. to 450° C.

6. The process as claimed in claim 1, wherein, in the preparation of the copper and zinc-containing catalytic material (B), the water-soluble copper salt and the water-soluble zinc salt are employed in an atomic ratio Cu/Zn of 4:6 to 7:3.

7. The process as claimed in claim 1, wherein, in the preparation of the copper and zinc-containing catalytic material (B), after the mixing step is completed, the mixture liquid containing the resultant precipitate is aged.

8. The process as claimed in claim 1, wherein the catalyst is recovered from the hydrogenate-decomposition reaction product mixture by filtering it.

9. The process as claimed in claim 1, wherein the carboxylic acid mixture comprises, as principal components, adipic acid, glutaric acid, and succinic acid and oxycaproic acid.

10. The process as claimed in claim 1, wherein the preparation of the copper and zinc-containing catalyst (B) is free from a reducing step with hydrogen.

11. The process as claimed in claim 1, wherein in the esterification of the carboxylic acid mixture, the esterifying alcohol is selected from methyl alcohol, ethyl alcohol, propyl alcohol, butyl alcohol, 1,4-butanediol, 1,5-pentanediol, and 1,6-hexanediol.

12. The process as claimed in claim 1, wherein, in the esterification of the carboxylic acid mixture, the esterifying alcohol is used in an amount of 1.2 to 1.5 times, in terms of hydroxy group equivalent of the alcohol, the acid value of the carboxylic acid mixture.

13. The process as claimed in claim 1, wherein the esterifying procedure is carried out at a temperature of 200° C. to 250° C. to such an extent that the resultant esterification product exhibits an acid value of 5 mg-KOH/g or less.

14. The process as claimed in claim 1, wherein the hydrogenate-decomposition reaction is carried out at a temperature of 250° to 300° C. under a hydrogen pressure of 150 to 300 kg/cm$^2$G.

15. The process as claimed in claim 1, wherein the catalyst is in the form of particles having a size of 1 to 100 μm and a median size of 15 to 25 μm.

16. The process as claimed in claim 1, wherein the catalyst is employed in an amount of 0.1 to 3.0% based on the weight of the esterification reaction product mixture prepared from the carboxylic acid mixture.

17. A process for producing diol compounds, higher alcohol compounds and aminoalcohol compounds, comprising the steps of;

esterifying a carboxylic acid with an esterifying alcohol, and hydrogenate-decomposing the resultant esterification product with hydrogen wherein the hydrogenate-decomposition of the esterification product with hydrogen is carried out in the presence of a catalyst comprising (A) copper and zinc-containing catalytic material prepared by mixing an aqueous solution containing a water-soluble copper salt and a water-soluble zinc salt with an aqueous solution containing at least one member selected from the group consisting of alkali metal carbonates, ammonium carbonate, alkali metal hydrogen carbonates and ammonium hydrogen carbonate to produce a precipitate comprising a water-insoluble basic copper and zinc carbonate mixture, reducing the precipitate with hydrogen, in a reduction gas containing the hydrogen at a temperature of 100° C. to 400° C., and contacting the resultant reduction product with an oxygen-containing gas.

18. The process as claimed in claim 17, wherein the carboxylic acid is selected from saturated and unsaturated, straight and branched chain carboxylic acids having 6 or more carbon atoms.

* * * * *